US009932608B2

(12) United States Patent
Thorsness et al.

(10) Patent No.: US 9,932,608 B2
(45) Date of Patent: Apr. 3, 2018

(54) METHOD FOR ENHANCED FERMENTATION THROUGH THE DESTRUCTION OF MITOCHONDRIAL DNA IN YEAST

(71) Applicant: University of Wyoming, Laramie, WY (US)

(72) Inventors: Peter E. Thorsness, Laramie, WY (US); Elizabeth A. Hiatt, Laramie, WY (US)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 14/558,124

(22) Filed: Dec. 2, 2014

(65) Prior Publication Data

US 2015/0152423 A1    Jun. 4, 2015

Related U.S. Application Data

(60) Provisional application No. 61/910,594, filed on Dec. 2, 2013.

(51) Int. Cl.
| | |
|---|---|
| C12N 15/113 | (2010.01) |
| C12P 7/06 | (2006.01) |
| C12N 1/19 | (2006.01) |
| C12N 15/81 | (2006.01) |

(52) U.S. Cl.
CPC ............... *C12P 7/06* (2013.01); *C12N 15/81* (2013.01); *Y02E 50/17* (2013.01)

(58) Field of Classification Search
CPC ...... C12N 2800/22; C12N 15/63; C12N 9/22; C12P 7/06
USPC .......................... 435/254.2, 254.11, 161, 199
See application file for complete search history.

(56) References Cited

U.S. PATENT DOCUMENTS

| 4,970,147 A | * | 11/1990 | Huala | ................... | C07K 14/195 435/252.3 |
| 2005/0019924 A1 | * | 1/2005 | Hitzeman | ............... | C12N 15/90 435/455 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340Whisstock et al., (Quarterly Reviews of Biophysics 2003, vol. 36 (3): 307-340.*
Kisselev L., (Structure, 2002, vol. 10: 8-9.*
Shiroma et al. (Appld Env Microbiol 2014, 80, pp. 1002-1012.*
Oner et al. (Yeast 2006, 23, pp. 849-856.*
Hutter et al. ((Appld Microbiol Biotecnol 1998, 49, pp. 511-516.*
Abe, Hiroko et al. "Ethanol-tolerant *Saccharomyces cerevisiae* strains isolated under selective conditions by over-expression of a proofreading-deficient DNA polymerase", Journal of Bioscience and Bioengineering, Mar. 24, 2009, vol. 108 No. 3, p. 199-204.
Abramova, Natalia et al. "Reciprocal Regulation of Anaerobic and Aerobic Cell Wall Mannoprotein Gene Expression in *Saccharomyces cervisiae*", Journal of Bacteriology, May 2001, vol. 183, No. 9, p. 2881-2887.
Agren, Rasmus et al. "Genome-scale modeling enables metabolic engineering of *Saccharomyces cerevisiae* for succinic acid production", Journal of Industrial Microbiology and Biotechnology, Apr. 23, 2013, Vol. 40, No. 7, p. 735-747.
Alper, Hal et al. "Enginerring Yeast Transcription Machinery for Improved Ethanol Tolerance and Production", Science, Dec. 8, 2006, vol. 314, p. 1565-1568.
Hibbs, Matthew A. et al. "Exploring the functional landscape of gene expression: directed search of large microarray compendia", Bioinformatics, Aug. 27, 2007, vol. 23, No. 20, p. 2692-2699.
Attardi, Guiseppe et al. "Biogenesis of Mitochondria", Annual Review of Cellular Biology, Ann. Rev. Cell Biol. 1988, Vol. 4, p. 289-331.
Bacman, S.R. et al., 2007. Modulating mtDNA heteroplasmy by mitochondria-targeted restriction endonucleases in a "differential multiple cleavage-site" model. Gene therapy, 14(18), pp. 1309-1318.
Bayona-Bafaluy, Marla Pilar et al. "Rapid directional shift of mitochondrial DNA heteroplasmy in animal tissues by a mitochondrially targeted restriction endo nuclease", PNAS, Aug. 15, 2005 vol. 102, No. 40 p. 14392-14397.
Becker, Jessica et. al. "A Modified *Saccharomyces cervisiae* Strain That Consumes L-Arabinose and Produces Ethanol", Applied and Environmental Microbiology, Jul. 2003, p. 4144-4150.
Benjaphokee, Suthee et al. "Highly efficient bioethanol production by a *Saccharomyces cerevisiae* strain with multiple stress tolerance to high temperature, acid and ethanol", New Biotechnology, Feb. 3, 2012, vol. 29, No. 3, p. 379-386.
Calahan, Dean et al. "Genetic Analysis of Desiccation Tolerance in *Saccharomyces cerevisiae*", Genetics, Oct. 2011, vol. 189, p. 507-519.
Carvalho-Netto, Osmar V. et. al. "A simple and effective set of PCR-based molecular markers for the monitoring of the *Saccharomyces cerevisiae* cell population during bioethanol fermentation", Journal of Biotechnology, Aug. 29, 2013, vol. 168 p. 701-709.
Chemier, Joseph, et. al. "Trends in microbial synthesis of natural products and biofuels", Article in Advances in Enzymology and Related Areas of Molecular Biology, Feb. 2009, p. 151-217.

(Continued)

*Primary Examiner* — Robert B Mondesi
*Assistant Examiner* — Mohammad Y Meah
(74) *Attorney, Agent, or Firm* — James M. Weatherly; Cochran Freund & Young LLC

(57) ABSTRACT

Methods for enhanced yeast fermentation of plant material through the genetic modification of yeast comprising stably integrating into a yeast an inducible promoter operably linked to a mitochondrial targeting signal as well as at least one restriction enzyme and inducing the expression of the at least one restriction enzyme, wherein the restriction enzyme targets and destroys the mitochondrial DNA of the yeast. DNA constructs comprising at least an inducible promoter operably linked to a mitochondrial targeting signal as well as at least one restriction enzyme for induced expression of at least one restriction enzyme for destruction of mitochondrial DNA as well as transgenic yeast expressing a DNA construct for destruction of mitochondrial DNA and enhanced fermentation, are also disclosed.

4 Claims, 8 Drawing Sheets

(56) References Cited

OTHER PUBLICATIONS

Choi, Gi-Wook, et. al. "Repeated-batch fermentation using flocculent hybrid, *Saccharomyces cerevisiae* CHFY0321 for efficient production of bioethanol", Appl. Microbiol Biotechnol, Mar. 25, 2009, vol. 84, p. 261-269.

Dikicioglu, Duygu, et. al. "Integration of Metabolic Modeling and Phenotypic Data in Evaluation and Improvement of Ethanol Production Using Respiration-Deficient Mutants of *Saccharomyces cerivisiae*", Applied and Environmental Microbiology, Jun. 22, 2008, vol. 74, No. 18, p. 5809-5816.

Fox, Thomas, "Guide to Yeast Genetics and Molecular Biology [10] Analysis and manipulation of yeast mitochondrial genes", Article in Methods in Enzymology, 1991, vol. 194, p. 149-165.

Francis, Brian R. et al. "Mutations in the Atp1p and Atp3p subunits of yeast ATP synthase differentially affect respiration and fermentation in *Saccharomyces cerevisiae*", J Bioenerg Biomembr, 2007, vol. 39, p. 127-144.

Garcia Sanchez, Rosa, "Improved xylose and arabinose utilization by an industrial recombinant *Saccharomyces cerevisiae* strain using evolutionary enginerring", Biotechnology for Biofuels, 2010, vol. 3, No. 13, 11 pages.

Ghiaci, Payam et al. "Physiological adaptations of *Saccharomyces cerevisiae* evolved for improved butanol tolerance", Biotechnology for Biofuels, 2013, vol. 6, No. 101, 12 pages.

Gonzalez-Ramos et al. "Genome-scale analyses of butanol tolerance in *Saccharomyces cerevisiae* reveal an essential role of protein degradation", Biotechnology for Biofuels, www.biotechnologyforbiofuels.com, 2013, vol. 6, No. 48, 18 pages.

Grant, Chris M. et al. "Mitochondrial function is required for resistance to oxidative stress in the yeast *Saccharomyces cerevisiae*", FEBS Letters 410, 1997, vol. 18740, p. 219-222.

Haffter, Pascal et al. "Nuclear Mutations in the Petite-Negative Yeast *Schizosaccharomyces pombe* Allow Growth of Cells Lacking Mitochondrial DNA", Genetics, Jun. 1992, vol. 131, p. 255-260.

Hanekamp, Theodor et al. "Inactivation of YME2/RNA12, Which Encodes an Integral Inner Mitochondrial Membrane Protein, Causes Increased Escape of DNA from Mitochondria to the NucleUs in *Saccharomyces cerevisiae*", Molecular and Cellular Biology, Mar. 7, 1996, vol. 16, No. 6, p. 2764-2771.

Hanekamp, Theodor et al. "Maintenance of Mitochondrial Morphology is Linked to Maintenance of the Mitochondrial Genome in *Saccharomyces cerevisiae*", Genetics, Nov. 2002, vol. 162, p. 1147-1156.

Hu, Jia et al. "Assessing chronological Aging in *Saccharomyces cerevisiae*", Methods Mol Biol., Jun. 2, 2014, vol. 965, p. 463-472.

Jin, Yong-Su et al. "*Saccharomyces cerevisiae* Engineered for Xylose Metabolism Exhibits a Respiratory Response", Applied and Environmental Microbiology, Nov. 2004, vol. 70, No. 11, p. 6816-6825.

King, Michael et al. "Isolation of Human Cell Lines Lacking Mitochondrial DNA", Methods in Enzymology, 1996, vol. 264, No. 27, p. 304-313.

Kukat, Alexandra et al. Generation of p0 cells utilizing a mitochondrially targeted restriction endonuclease and comparative analyses, Nucleic Acids Research, Mar. 19, 2008, vol. 36, No. 7, p. 1-10.

Lai, Liang-Chuan et al. "Dynamical Remodeling of the Transcriptome during Short-Term Anaerobiosis in *Saccharomyces cerevisiae*: Differential Response and Role of Msn2 and/or Msn4 and Other Factors in Galactose and Glucose Media," Molecular and Cellular Biology, May 2005, p. 4075-4091.

Liu Z. Lewis, "Genomic adaptation of ethanologenic yeast to biomass conversion inhibitors," Appl Microbiol Biotechnol, 2006, vol. 73, p. 27-36.

Lu, Ying et al. "Improvement of robustness and ethanol production of ethanologenic *Saccharomyces cerevisiae* under co-stress of heat and inhibitors", J Ind Microbiol Biotechnol (2012) vol. 39, p. 73-80.

Luo, Zongli et al. "Functional analyses of PAU genes in *Saccharomyces cerevisiae*", Microbiology (2009), vol. 155, p. 4036-4049.

Marathe, Sudhir et al. "Vectors with the gus reporter gene for identifying and quantitating promoter regions in *Saccharomyces cerevisiae*", Gene (1995) vol. 154, p. 105-107.

McKinlay, James B. et al. "Prospects for a bio-based succinate industry", Appl Microbiol Biotechnol (2007), vol. 76, p. 727-740.

Mireau, H. et al. "Expression of Barstar as a selectable marker in yeast mitochondria", Mol Gen Genomics (2003), vol. 270, p. 1-8.

Ocampo, Alejandro et al. "Mitochondrial Respiratory Thresholds Regulate Yeast Chronological Life Span and its Extension by Caloric Restriction", Cell Metabolism Article in Cell Press, Jul. 3, 2012, vol. 16, p. 55-67.

Pedersen, Peter L. "Mitochondrial Events in the Life and Death of Animal Cells: A Brief Overview", Journal of Bioenergetics and Biomembranes, 1999, vol. 31, No. 4, p. 291-304.

Sakamoto, Takatoshi et al. "Direct ethanol production from hemicellulosic materials of rice straw by use of an engineered yeast strain codisplaying three types of menicellulolytic enzymes on the surface of xylose-utilizing *Saccharomyces cerevisiae* cells", Journal of Biotechnology, 2012, vol. 158, p. 203-210.

Sauer, Brian "Functional Expression of the cre-lox Site-Specific Recombination System in the Yeast *Saccharomyces cerevisiae*", Molecular and Cellular Biology, Jun. 1987, vol. 7, No. 6, p. 2087-2096.

Smith, Christopher P. "Formation of an Energized Inner Membrane in Mitochondria with a y-Deficient F1-ATPase", Eukaryotic Cell, Dec. 2005, vol. 4, No. 12, p. 2078-2086.

van Vleet, JH et al. "Yeast metabolic engineering for hemicellulosic ethanol production", Current Opinion in Biotechnology, 2009, vol. 20, p. 300-306.

Wohl, Thorsten et al. "The HYP2 gene of *Saccharomyces cerevisiae* is essential for aerobic growth: characterization of different isoforms of the hypusine-containing protein Hyp2p and analysis of gene disruption mutants" Mol Gen Genet, 1993, vol. 241, p. 305-311.

Zhu, J.Y. et al."Pretreatment of woody biomass for biofuel production: energy efficiency, technologies and recalcitrance" Appl Microbiol Biotechnol, 2010, vol. 87, p. 847-857.

Gueldener, U. et al. "A second set of loxP marker cassettes for Cre-mediated multiple gene knockouts in building yeast", Nucleic Acis Research, 2002, vol. 30, No. 6, p. 2-8.

Kominsky, Douglas J. et al. "Genetic and Biochemical Basis for Viability of Yeast Lacking Mitochondrial Genomes", Mitochondrial Membrane Potential in p0 Yeast, p. 1595-1604.

Lewis, J.A. et al., 2010. Exploiting natural variation in *Saccharomyces cerevisiae* to identify genes for increased ethanol resistance. Genetics, 186(4), pp. 1197-1205.

Kalifa, Lidza et al. "Mitochondrial Genome Maintenance: Roles for Nuclear Nonhomologous End-Joining Proteins in *Saccharomyces cerevisiae*", Genetics, Mar. 2012, vol. 190, p. 951-964.

Ter Linde, J.J.M et al. "Genome-Wide Transcriptional Analysis of Aerobic and Anaerobic Chemostat Cultures of *Saccharomyces cerevisiae*", Journal of Bacteriology, Dec. 1999, vol. 181, No. 24, p. 7409-7413.

Erickson, Brent et al. "Perspective on opportunities in industrial biotechnology in renewable chemicals", Biotechnology Journal, 2012, vol. 7, p. 176-185.

Fabrizio, Paola et al. "The chronological life span of *Saccharomyces cerevisiae*", Aging Cell, 2003, vol. 2, p. 73-81.

Westermann, Benedikt et al. "Mitochondria-targeted green fluorescent proteins: convenient tools for the study of organelle biogenesis in *Saccharomyces cerevisiae*", Yeast, 2000, vol. 16, p. 1421-1427.

Welch, Aaron Z. et al. "TOR and RAS pathways regulate desiccation tolerance in *Saccharomyces cerevisiae*", Molecular Biology of the Cell, Jan. 15, 2013, vol. 24, p. 113.

Oner, Ebru Toksoy et al. "Production of Ethanol from Starch by Respiration-Deficient Recombinant *Saccharomyces cerevisiae*", Applied and Environmental Microbiology, Oct. 2005, vol. 70, No. 10, p. 6443-6445.

(56) References Cited

OTHER PUBLICATIONS

Teixeira, Miguel C. et al. "Genome-Wide Identification of *Saccharomyces cerevisiae* Genes Required for Maximal Tolerance to Ethanol", Applied and Environmental Microbiology, Sep. 2009, vol. 75, No. 18, p. 5761-5772.
Stanley, D. et al. "The ethanol stress response and ethanol tolerance of *Saccharomyces cerevisiae*", Journal of Applied Microbiology, Dec. 11, 2009, vol. 109, p. 13-24.
Rapaport, D. et al. "Fzo1p is a Mitochondrial Outer Membrane Protein Essential for the Biogenesis of Functional Mitochondria in *Saccharomyces cerevisiae*", The Journal of Biological Chemistry, Aug. 7, 1998, vol. 273, No. 32, p. 20150-20155.
Bera, A.K. et al., 2011. A genetic overhaul of *Saccharomyces cerevisiae* 424A(LNH-ST) to improve xylose fermentation. Journal of industrial microbiology & biotechnology, 38(5), pp. 617-626.
Hu, X.H. et al. "Genetic Dissection of Ethanol Tolerance in the Budding Yeast *Saccharomyces cerevisiae*", Genetics, Mar. 2007, vol. 175, p. 1479-1487.
Cohen et al. Introduction and repression of DAN1 and the family of anaerobic mannoprotein genes in *Saccharomyces cerevisiae* occurs through a complex array of regulatory sites, Nucleic Acids Research, (2001) vol. 29, No. 3: 799-808.
Rintala et al. Transcriptional Responses of *Saccharomyces cerevisiae* to Shift from Respiratory and Respirofermantative to Fully Fermentative Metabolism, Journal of Integrative Biology, (2011) vol. 15, Nos. 7-8: p. 461-476.
Mireau et al. Expression of Barstar as a selectable marker in yeast mitochondria. Mol. Gen. Genomics (2003) 270:1-8.
Donahue et al. Expression of bacterial endonucleases in *Saccharomyces cerevisiae* mitochondria, Mitochondrion 2 (2002) 47-57.
Curran et al. Use of High Capacity Terminators in *Saccharomyces cerevisiae* to Increase mRNA half-life and Improve Gene Expression Control for Metabolic Engineering Applications, Metab Eng. Sep. 1, 2013: 88-97.

* cited by examiner

Rho+ yeast cultured in rich glucose media in the presence of 2.5 mM potassium cyanide (KCN), a respiratory inhibitor showing growth curves for yeast cultures that have been treated with KCN at the indicated points in their fermentations.

METHOD FOR ENHANCED FERMENTATION THROUGH THE DESTRUCTION OF MITOCHONDRIAL DNA IN YEAST

CROSS REFERENCE TO RELATED APPLICATIONS

The present application claims priority of U.S. Provisional Patent Application Ser. No. 61/910,594, filed on Dec. 2, 2013, entitled "METHOD FOR ENHANCED FERMENTATION THROUGH THE DESTRUCTION OF MITOCHONDRIAL DNA IN YEAST," the entire contents are herein incorporated by reference for all they teach and disclose.

BACKGROUND

All publications cited in this application are herein incorporated by reference.

The budding yeast *Saccharomyces cerevisiae* is routinely used in fermentations that produce biofuels and other high-value products. This yeast is capable of fermentation of hexoses (e.g., glucose) in the absence or presence of oxygen. Pyruvate is the theoretical endpoint of glycolysis, but continued fermentative metabolism reduces pyruvate to lactate or reduces the pyruvate derivative acetaldehyde to ethanol. The conversion to ethanol is typically favored in *S. cerevisiae*, although genetic modifications have yielded strains that have a metabolic endpoint of isobutanol or other commercially valuable products. In the presence of oxygen, pyruvate can alternatively be subjected to complete oxidation by enzymes of the tricarboxylic acid (TCA) cycle; the electrons stripped from pyruvate are ultimately donated to oxygen. Consequently, one outcome of glucose metabolism in yeast (and many other organisms) is the coupling of glycolysis (production of pyruvate) to the oxidative degradation of pyruvate with the ultimate transfer of electrons to oxygen (cellular respiration), resulting in the generation of ATP. If glucose is plentiful, *S. cerevisiae* metabolizes glucose largely (but not exclusively) by fermentation as it provides the most rapid way to gain sufficient energy for biosynthesis and cell growth. As glucose becomes limiting, cellular respiration is engaged to extract energy from alternative carbon sources including the materials that were the produced during the fermentative phase of growth.

Commercial strains of yeast have been engineered and selected to grow vigorously in preparatory phases of the industrial fermentation cycle. Most domestic fuel ethanol plants fermenting a corn feedstock purchase yeast in bulk from a wholesale supplier, often as a "dry active yeast" or "cream yeast". In either case, preparations are produced on a large scale, beginning with small-scale "seed" propagation, and scaling to multi-thousand liter fermenters. In order to enhance biomass, the yeast are cultivated in a highly aerobic environment. Ultimately the yeast are harvested and prepared for sale and shipment to fuel ethanol plants. There, tens of kilograms of the purchased yeast stock are propagated aerobically using the corn mash to enhance the number of yeast cells that are added to the large (40,000 liter and larger) fermenters. This is the production phase of fermentation where anaerobic conditions induce the production of ethanol, isobutanol or other high-value bio-based chemicals.

The foregoing examples of related art and limitations related therewith are intended to be illustrative and not exclusive, and they do not imply any limitations on the inventions described herein. Other limitations of the related art will become apparent to those skilled in the art upon a reading of the specification and a study of the drawings.

SUMMARY

The following embodiments and aspects thereof are described and illustrated in conjunction with systems, tools and methods, which are meant to be exemplary and illustrative, not limiting in scope.

An embodiment of the present invention may comprise a method for enhanced fermentation through the genetic modification of yeast comprising: stably integrating into a yeast an inducible promoter coding sequence operably linked to a mitochondrial targeting signal coding sequence, wherein said mitochondrial targeting signal coding sequence is operably linked to an at least one restriction enzyme coding sequence, inducing the expression of the at least one restriction enzyme, wherein said at least one restriction enzyme targets and destroys the mitochondrial DNA of the yeast, and inducing enhanced fermentation by said yeast.

An embodiment of the present invention may comprise a DNA construct for enhanced yeast fermentation through the genetic modification of yeast comprising: an inducible promoter, at least one restriction enzyme wherein the inducible promoter is operably linked to the at least one restriction enzyme, and at least one mitochondrial targeting signal coding sequence.

An embodiment of the present invention may comprise a transgenic yeast having a DNA construct stably integrated into the transgenic yeast under conditions suitable for expression of the DNA construct in transgenic yeast, wherein the DNA construct comprises an inducible promoter, a mitochondrial targeting signal coding sequence and at least one restriction enzyme and wherein the DNA construct expresses a restriction enzyme targeted at the mitochondrial DNA of the transgenic yeast.

In addition to the example, aspects and embodiments described above, further aspects and embodiments will become apparent by reference to the drawings and by study of the following descriptions, any one or all of which are within the embodiments of the invention. The summary above is a list of example implementations, not a limiting statement of the scope of the embodiments of the invention.

BRIEF DESCRIPTION OF THE FIGURES

The accompanying figures, which are incorporated herein and form a part of the specification, illustrate some, but not the only or exclusive, example embodiments and/or features. It is intended that the embodiments and figures disclosed herein are to be considered illustrative rather than limiting.

DETAILED DESCRIPTION

Embodiments of the present disclosure include methods for enhancing yeast fermentation of plant material through the genetic modification of yeast, where the term "yeast" includes but is not limited to *Saccharomyces cerevisiae*. The methods for enhancing yeast fermentation described in the present disclosure proceed by means of the induced destruction of the mitochondrial DNA of the yeast, through stably integrating into yeast a restriction enzyme operably linked to an inducible promoter. The inducible promoter may be an oxygen sensitive promoter which induces expression of the restriction enzyme once the level of oxygen in the fermentation process reaches a certain level, such as zero, or in the presence of anaerobic conditions. The expressed restriction enzyme targets the mitochondria DNA of the yeast and induces the complete loss of mitochondrial DNA from the yeast genome.

One or more embodiments of the present disclosure include methods for increasing the ethanol production of yeast by stably introducing a construct into a transgenic yeast where the construct comprises an inducible promoter such as an anaerobic or oxygen sensitive promoter, where an example may be the PAU20 promoter operably linked to a restriction enzyme, such as the MseI restriction enzyme, recognizing the TTAA sequence of DNA.

Figure 1:
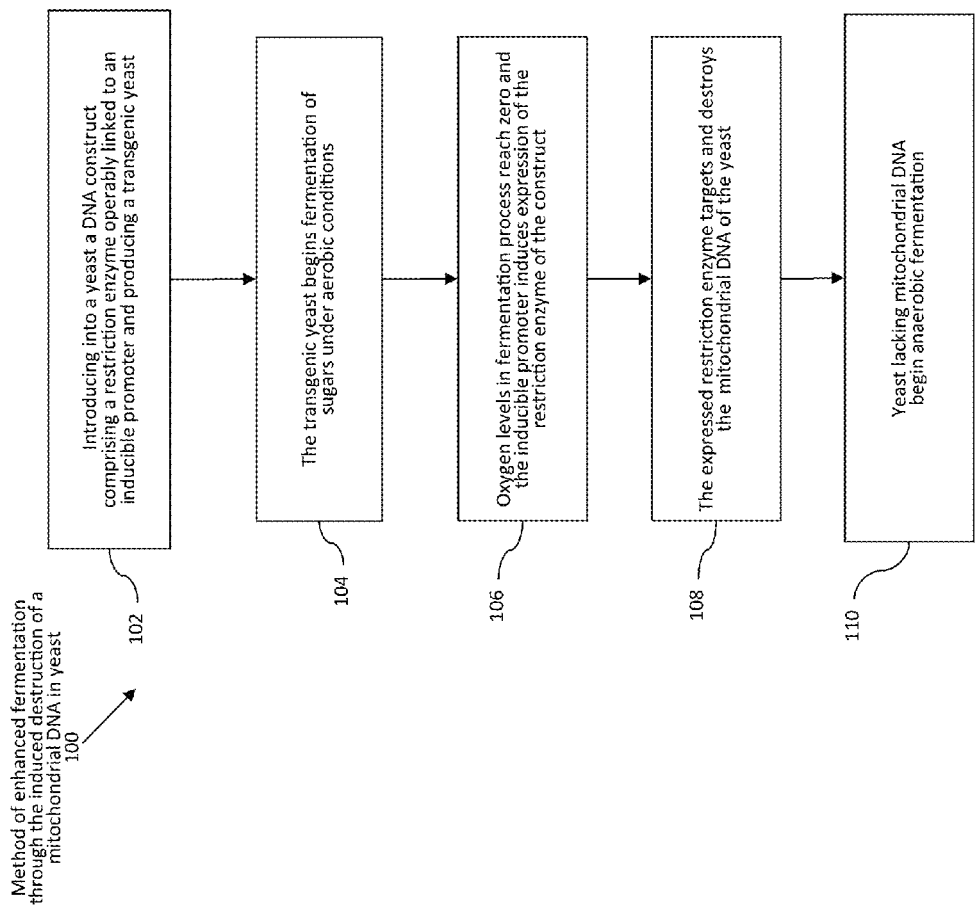
FIG. 1 is a flow diagram of a method of enhanced fermentation in yeast through the induced destruction of mitochondrial DNA in yeast.

FIG. 1 provides a flow diagram of an example method of the present disclosure 100. As shown in step 102, a DNA construct is stably incorporated into the nuclear genome of a yeast. The DNA construct comprises at least one restriction enzyme, such as the MseI restriction enzyme and is operably linked to an inducible promoter, such as the anaerobic promoter PAU20 and a transgenic yeast capable of induced expression of the restriction enzyme is produced. The DNA construct may also include a selectable marker, such as a drug resistance marker such as that encoded by the KanMX module. In step 104, the transgenic yeast begins fermentation of hexoses under aerobic conditions. In step 106, once the oxygen level in the fermentation process reaches a certain level, such as zero, or anaerobic conditions, the inducible promoter operably linked to the restriction enzyme induces expression of the restriction enzyme. In step 108, the expressed restriction enzyme targets the mitochondrial compartment of the yeast, inducing the controlled loss of the mitochondrial DNA. In step 110, with the loss of the mitochondrial DNA, the yeast begins anaerobic fermentation.

Figure 2A:
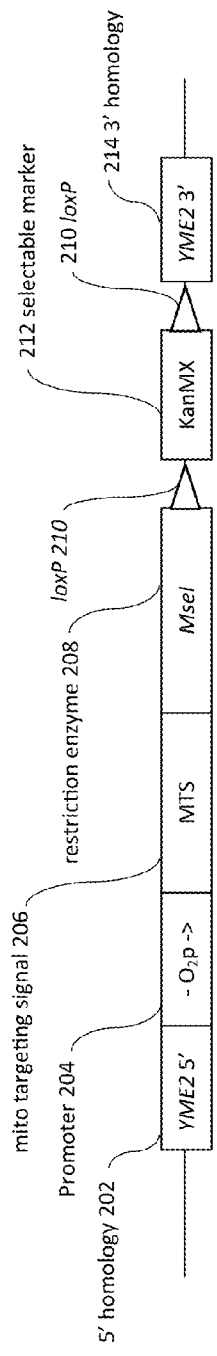
FIG. 2a is a schematic diagram of a DNA construct for the destruction of yeast mitochondrial DNA.
Figure 2B:
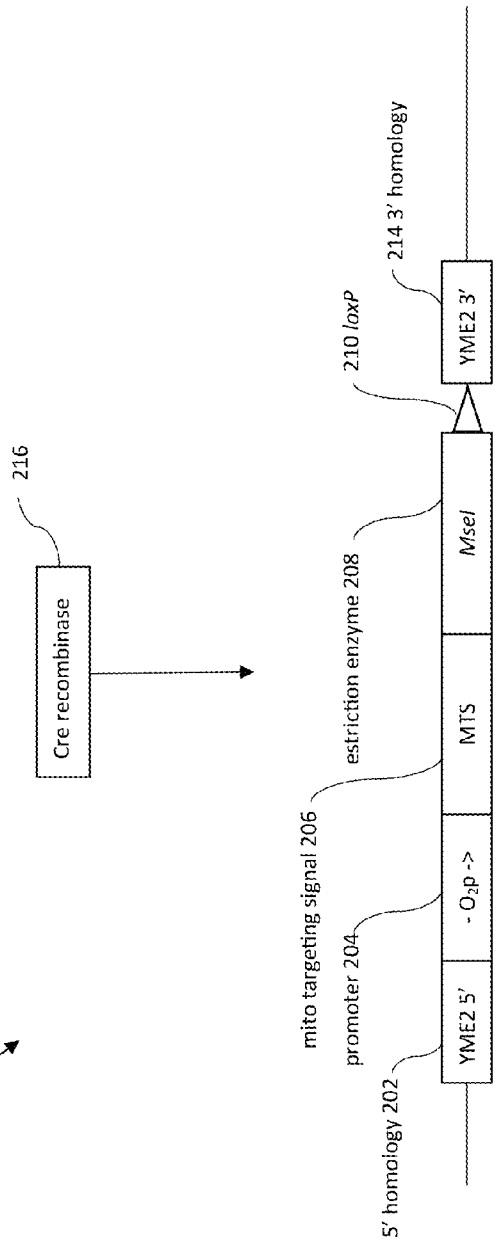
FIG. 2b is a schematic diagram of a DNA construct for the destruction of yeast mitochondrial DNA following the removal of the selectable marker via Cre recombinase.

As shown in FIG. 1 and discussed further herein and in FIGS. 2a and 2b, the induction of respiratory incompetence during growth conditions corresponding to the production phase of industrial fermentations increases the production of products such as ethanol. The methods described herein and shown in FIGS. 1, 2a and 2b create gene fusions between promoters induced by anaerobic conditions and structural genes encoding mitochondrially-targeted restriction enzymes. The restriction enzymes, produced only during anaerobic fermentation, lead to a rapid loss of mitochondrial respiratory activity and enhanced fermentative output.

In an embodiment of the present description, the transgenic yeast produced from the methods of the present disclosure are expected to have a 1% to 5% rho° rate in the presence of oxygen but will be 100% rho° by the midpoint of an anaerobic fermentation. Specifically, the methods provided enhance fermentation by as much as 25% via specific genetic modifications of commercially proven yeast strains. Use of yeast strains developed through methods described herein enable more efficient conversion of sugars into biofuels and high-value gateway chemicals, driving down operating costs through more efficient use of the feedstock used in fermentation, whether it is derived from cellulosic biomass or corn.

In an embodiment of the present disclosure and described in further detail below, the methods described herein provide an alternative path to harnessing the enhanced fermentation properties of rho° yeast (yeast lacking mitochondrial DNA) while avoiding the negative phenotypic properties associated with the loss of respiration. Modifying industrial strains of yeast using the methods described herein induce respiratory incompetence in yeast through the destruction of mitochondrial DNA during the production phase of fermentation, making practical the use of respiration-deficient yeast to enhance production of biofuels and other high-value products. The introduction of condition-dependent dominant genetic elements, such as but not limited to oxygen dependent inducible promoters operably linked to restriction enzyme coding sequences, broadly inhibit mitochondrial respiration into industrial strains of yeast that are optimized for tolerance to environmental inhibitors, modified to ferment a diversity of saccharides and produce advanced biofuels and high-value products is a major objective of this research and development effort.

FIG. 2a provides a schematic of an example gene fusion containing a DNA construct for the induced expression of one or more restriction enzymes for targeting and destruction of mitochondrial DNA in yeast, 200. As shown in FIG. 2a, a construct is provided, where starting at the 5' end 202 of the YME2 gene of yeast, an anaerobic inducible promoter coding sequence 204 is provided, identified as —O$_2$p, an example inducible promoter being the anaerobic promoter PAU20. A mitochondrial targeting signal coding sequence is provided, identified as Mito Targeting Signal 206. A restriction enzyme coding sequence, an example being the MseI restriction enzyme 208, is provided. The integrants of the gene fusion are identified by virtue of the gene fusion containing a linked dominant selectable marker, in this instance one providing drug resistance is used, such as that encoded by the KanMX module 212, a commonly used selectable marker in yeast. This drug resistance marker 212 is flanked on each side by loxP 210 coding sequences, the site of action for the Cre recombinase (see Sauer 1987. *Molecular and cellular biology,* 7(6), pp. 2087-2096) on the 3' homology end 214. Each of these components is operably linked to the next, i.e., the inducible promoter coding sequence 204, —O$_2$p, is operably linked to the 5' end of the Mito Targeting Signal coding sequence 206, the Mito Targeting Signal coding sequence 206 is operably linked to the 5' end of the restriction enzyme coding sequence 208, which may be operably linked to the 5' end of the selectable marker protein coding sequence 212. The construct of FIG. 2a is then integrated into a yeast and yeast expressing the restriction enzyme targeting the yeast's mitochondrial DNA are generated. As will be understood by one skilled in the art, other versions of this construct may be created, including but not limited to constructs as described above but lacking the selectable marker. All DNA manipulations are performed using standard techniques (see Sambrook, et al., *Molecular Cloning*, 2nd Ed., Cold Spring Harbor Laboratory Press, Cold Spring Harbor, N.Y. (1989)). Restriction and DNA modification enzymes may be purchased from New England Biolabs unless otherwise noted. Plasmid DNA is prepared from *E. coli* by boiling lysis (Sambrook et al., (1989).

As shown in FIG. 2b, once the integrants of the construct of FIG. 2a have been identified, the Cre recombinase 216 is introduced on a plasmid and yeast lacking the drug selection marker due to action of Cre at the loxP 210 sites and also lacking the unstable plasmid (easily identified via replica plate screening) are isolated and fully characterized. This is shown in FIG. 2b as the inducible promoter coding sequence 204, —O$_2$p, operably linked to the 5' end of the Mito Targeting Signal coding sequence 206, which is operably linked to the 5' end of the restriction enzyme coding sequence 208.

As discussed and shown in FIGS. 1, 2a and 2b, the example gene fusion of FIG. 2a and FIG. 2b composed of an anaerobic promoter drives the expression of a mitochondrially-targeted restriction enzyme. This genetic construct is integrated into a structural gene of the yeast, such as the YME2 structural gene and allows for the efficient analysis of alternative promoters and restriction enzymes. Further, the design of the construct allows for the removal of the dominant selectable (drug resistance) marker, making it immediately available for introduction into production strains of yeast.

As further shown in FIG. 2a and FIG. 2b, to insure the stable transmission of a genetic element that has selective growth disadvantages, the genetic element is integrated on a chromosome rather than propagate it on an inherently unstable extrachromosomal genetic element. There are a plethora of chromosomal sites to which the gene fusion can be targeted, however the YME2 gene of yeast is conserved throughout the fungi, behaves recessively when one copy of the gene is deleted in a diploid strain, and has a subtle phenotype when the null allele is homozygous (Hanekamp & Thorsness 1996. *Molecular and cellular biology*, 16(6), pp. 2764-2771). The YME2 gene product affects the structure of mitochondria DNA, rendering YME2 mutant yeast more susceptible to nuclease digestion in isolated and permeablized mitochondria. Hence, targeting the gene fusion to YME2 will not alter important growth phenotypes and may make mitochondrial DNA more susceptible to restriction enzyme digestion. Finally, it is important to target the gene fusion to a structural gene rather than an intragenic region to allow the constructs described herein to be functional in a variety of yeast strains that may be somewhat genetically diverse (Carvalho-Netto et al. 2013. *Journal of biotechnology*). Efficient and precise targeting of the gene fusion integration is optimized if the recombination machinery has extensive homology to recognize, a feature most likely found in a conserved structural gene as compared to an intragenic region.

As shown in FIG. 2a and FIG. 2b, the construction of the gene fusion described herein is straightforward. However, other expression systems, some unregulated, for the expression of restriction enzymes in eukaryotic cells may be used in the methods described herein and they all involve use of bacterial shuttle vectors in their creation. Additionally, the methods described herein may be altered to place the selectable marker 212 shown in FIG. 2a bordered by loxP 210 sites internal to the fusion gene, preventing expression of the restriction enzyme 208 until the disrupting selectable marker 212 is excised by exposure to Cre recombinase 216. In this instance, the restriction enzyme 208 structural gene would not be functional until after integration of the construct into the chromosome of yeast. If lethality of the integrated fusion gene in yeast is identified, the modular nature of the construct allows for the incorporation of alternative promoters such as DAN1 (Abramova et al. 2001. *J. Bacteriol.*, 183(9), pp. 2881-2887), ANB1 (Linde et al. 1999 *J. Bacteriol.*, 181(24), pp. 7409-7413; Wöhl et al. 1993 *Mol Gen Genet*, 241(3-4), pp. 305-311)) and/or other restriction enzymes such as EcoRI (Kukat et al. 2008 *Nucleic Acids Res*, 36(7), pp. e44-e44), ScaI (Bacman et al. 2007. *Gene therapy*, 14(18), pp. 1309-1318).

In the unlikely event that DNA restriction enzymes prove ineffective at creating rho° yeast, the Barnase/Barstar system could be employed (Mireau et al. 2003. *Mol Genet Genomics*, 270(1), pp. 1-8), directing the RNAse Barnase to mitochondria under transcription control of an anaerobic promoter as described above, with the inhibitor Barstar expressed under control of a promoter that is active only in the presence of oxygen such as the ROX1 promoter (Lai et al. 2005. *Molecular and cellular biology*, 25(10), pp. 4075-4091). In this system, barnase would only be expressed and directed to mitochondria in hypoxic conditions and barstar would assure tight regulation. Barnase directed to mitochondria and not inhibited by barstar quantitatively gives rise to rho-/rho° yeast (Mireau et al. 2003).

Figure 3A:
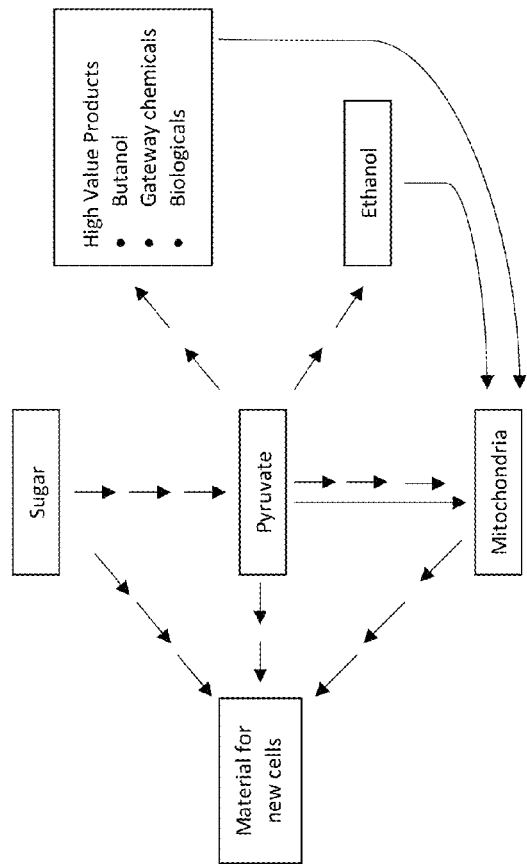
FIG. 3a is a diagram showing normal yeast mitochondrial production in yeast.
Figure 3B:
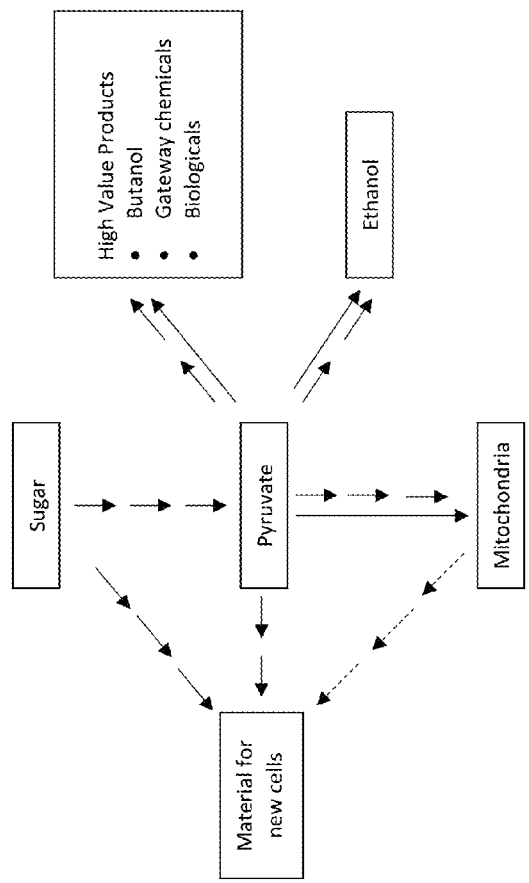
FIG. 3b is a diagram showing production of yeast cells lacking mitochondrial DNA.

For commercial purposes, complete oxidation of glucose to carbon dioxide and water is undesirable as it diverts precious carbon and electrons from pathways that lead to desired products. Altered mitochondrial function enhances fermentation outputs where normal mitochondrial function, shown in FIG. 3a, drains product and precursors, limiting product accumulation, but cells grow well. While as shown in FIG. 3b, yeast cells lacking mitochondrial respiration produce product at higher levels but have poorer cell growth.

Oxidation of pyruvate in yeast requires a functional mitochondrial electron transport chain. The passage of electrons through the electron transport chain is coupled to the establishment of a proton gradient across the inner mitochondrial membrane. This proton gradient is then used for a number of important mitochondrial processes. The most obvious use of the proton gradient is to power the synthesis of ATP via the mitochondrial ATP synthase. The transport of metabolites and proteins across the inner mitochondrial membrane is also dependent upon the membrane potential established by the proton gradient and is in fact essential for eukaryotic cell viability. It is possible to completely inhibit mitochondrial ATP synthase as ATP generated by glycolysis allows cells to remain viable; however, if the electrical gradient across the mitochondrial membrane is dissipated, cells will die because essential biochemical pathways housed in the mitochondrial matrix are no longer functional (Pedersen 1999. *J Bioenerg Biomembr*, 31(4), pp. 291-304).

Figure 4A:
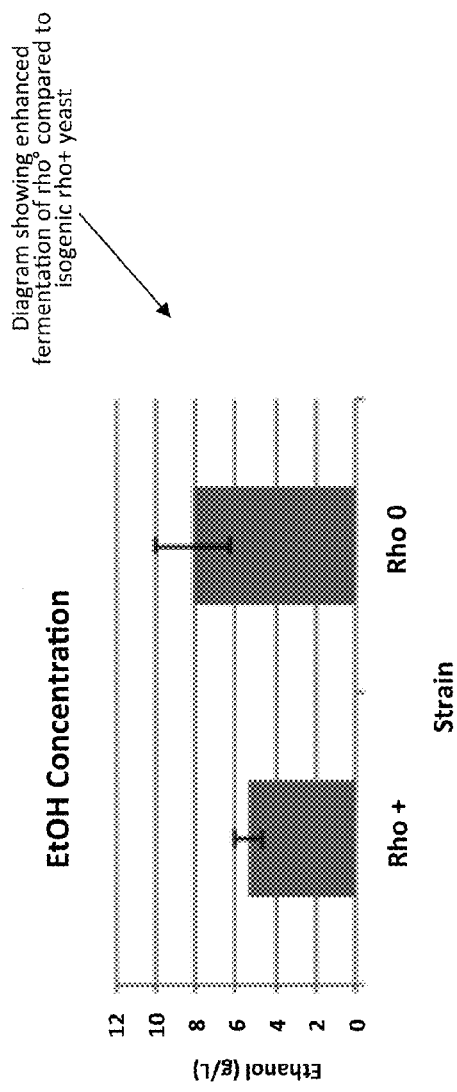
FIG. 4a is a diagram showing enhanced fermentation of rho° yeast (lacking mitochondrial DNA) compared to isogenic rho$^+$ yeast (with mitochondrial DNA).

The mitochondrial genome encodes essential components of the electron transport chain. Yeast that lack mitochondrial DNA (mtDNA) are called rho° yeast; these strains can only grow by fermentation (Fox et al. 1991). In rho° yeast, the electrical potential across the mitochondrial membrane is generated by the electrogenic exchange of ATP for ADP across the membrane rather than by the electron transport chain (Attardi & Schatz 1988). Although the magnitude of the mitochondrial membrane potential in rho° yeast is substantially lower than that found in yeast that contain an intact mitochondrial genome (rho$^+$ yeast), it is sufficient to maintain at least minimally functional mitochondria (Kominsky et al. 2002. *Genetics,* 162(4), pp. 1595-1604). Interestingly, rho° yeast have enhanced fermentative outcomes compared to isogenic rho⁺ yeast, as discussed in FIGS. 4a and 4b, (Dikicioglu et al. 2008. *Appl. Environ. Microbiol.,* 74(18), pp. 5809-5816; Toksoy Oner et al. 2005. *Applied and Environmental Microbiology,* 71(10), pp. 6443-6445), offering gains in product accumulation that would normally be seen as hugely advantageous. However, rho° yeast do not grow as rapidly as rho⁺ yeast on rich glucose media, with the growth rate of rho° yeast diminished by as much as 40% compared to rho⁺ yeast (Francis et al. 2007. *J Bioenerg Biomembr,* 39(2), pp. 127-144). This decrease in robustness has prevented the adoption of respiratory-deficient yeast in commercial fermentations.

Yeast mitochondrial DNA encodes for eight (8) proteins, 22 tRNAs and two rRNAs. Mutational inactivation of any of these genes completely abrogates electron transport and oxidative phosphorylation. Furthermore, mutations or poisons that prevent transcription or translation lead to rearrangement and deletion of the mitochondrial genome, and in the most extreme cases to its complete loss (Fox et al. 1991). Growth of most eukaryotic cells in the presence of the DNA intercalating reagent ethidium bromide induces the loss of mitochondrial DNA (Haffter & Fox 1992; King & Attardi 1996. *Methods Enzymol.,* 264, pp. 304-313). Recently in an attempt to manipulate the copy number, affect recombination, or alter the distribution of heteroplasmic mitochondrial DNA in cells, DNA restriction enzymes have been targeted to mitochondria (Bayona-Bafaluy et al. 2005. *Proc. Natl. Acad. Sci. USA,* 102(40), pp. 14392-14397; Kalifa et al. 2012 *Genetics,* 190(3), pp. 951-964; Kukat et al. 2008). Particularly relevant is the use of the common restriction enzyme EcoRI, targeted to mitochondria from a nuclear encoded gene, to induce the complete loss of mitochondrial DNA in mammalian cells (Kukat et al. 2008). This treatment creates rho° cells in a rapid and efficient manner. While at least one instant of a restriction enzyme targeted to mitochondria of yeast is in the literature, it was done in a way that precluded the complete loss of mitochondrial DNA (Kalifa et al. 2012). Yeast mitochondrial DNA is easily manipulated by treatment with ethidium bromide and many genetic tools, so no effort has been made to destroy mitochondrial DNA by a mitochondrially targeted restriction enzyme. Placed under the control of an oxygen sensitive promoter, a mitochondrially-targeted restriction enzyme is an effective inducer of the respiration incompetence that is beneficial during production fermentation.

Rho° yeast lack mitochondrial DNA and have enhanced fermentative outcomes with respect to the yield of ethanol production (Dikicioglu et al. 2008; Toksoy Oner et al. 2005), presumably because available pyruvate is not lost to oxidation. Despite this advantage, rho⁺ yeast are preferred for fermentation because they grow more robustly than rho° yeast (see FIGS. 4a and 4b). Furthermore, rho° yeast respond less favorably to environmental stresses than does isogenic rho⁺ yeast. If rho⁺ yeast exhaust their carbon source, they typically have a prolonged "chronological life span", surviving for days in the spent media with virtually no cell death (Fabrizio & Longo 2003. *Aging cell,* 2(2), pp. 73-81; J. Hu et al. 2013. *Methods in molecular biology (Clifton, N.J.),* 965 (Chapter 30), pp. 463-472). However, rho° yeast are profoundly sensitive to carbon source depletion, dying rapidly with almost complete inviability achieved over the course of a few days, a time period when there is no loss of viability for similarly starved rho⁺ yeast (Francis et al. 2007; Ocampo et al. 2012. *Cell Metabolism,* 16(1), pp. 55-67). Similarly, yeast compromised for respiratory activity are very sensitive to desiccation, with preparations of desiccated rho° yeast having but 1 in a million survive. In contrast, rho⁺ yeast are extremely resistant to desiccation with only a 50% loss in viability (Calahan et al. 2011. *Genetics,* 189(2), pp. 507-519). The major suppliers of yeast to industries that produce fuel ethanol often prepare their product as "dry active yeast", meaning it has been desiccated for storage and transport, or "cream yeast" meaning they're in a stable, dense stationary phase. Either of these methods when used to prepare and supply yeast on a commercial scale make it impractical to use rho° yeast for industrial scale fuel ethanol fermentations.

As discussed above, FIG. 4a provides a diagram showing enhanced fermentation of rho° yeast compared to isogenic rho⁺ yeast where the indicated strains of yeast were grown in rich glucose media to stationary phase (glucose exhausted) and the amount of ethanol generated was measured by monitoring the conversion of NAD+ to NADH in an enzyme-linked assay.

Figure 4B:
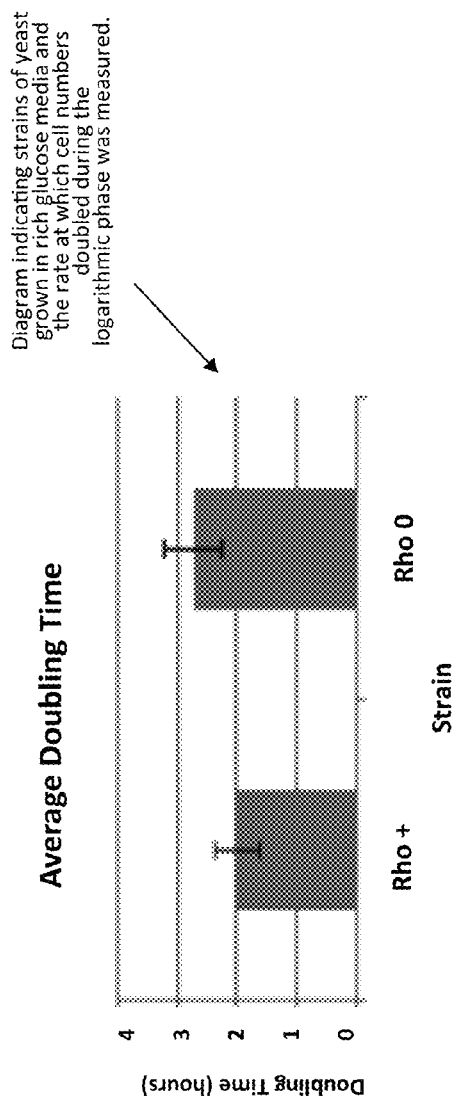
FIG. 4b is a diagram showing enhanced fermentation and growth of rho° compared to isogenic rho+ yeast.

FIG. 4b is a diagram indicating strains of yeast were grown in rich glucose media and the rate at which cell numbers doubled during the logarithmic phase was measured.

The methods and constructs described herein may be added to any commercial *S. cerevisiae* yeast strain to induce the controlled loss of mitochondrial DNA through the targeting of a DNA restriction enzyme to the mitochondrial compartment. The loss of mitochondrial DNA and subsequently respiration is coincident with the production phase of industrial fermentation, which takes place anaerobically. As evidenced in FIGS. 5a and 5b, respiratory poisons such as cyanide could be added to fermentations to enhance fermentative output. However, chemical additives on such a scale add significant cost and, more importantly, the addition of metabolic poisons would create significant safety and remediation problems and ruin an important bioproduct of industrial fermentations, the livestock feed generated from the left over solids. Consequently, the construction of a genetic switch that is activated by the environmental conditions used during the production phase of commercial fermentations is most desirable.

Figure 5A:
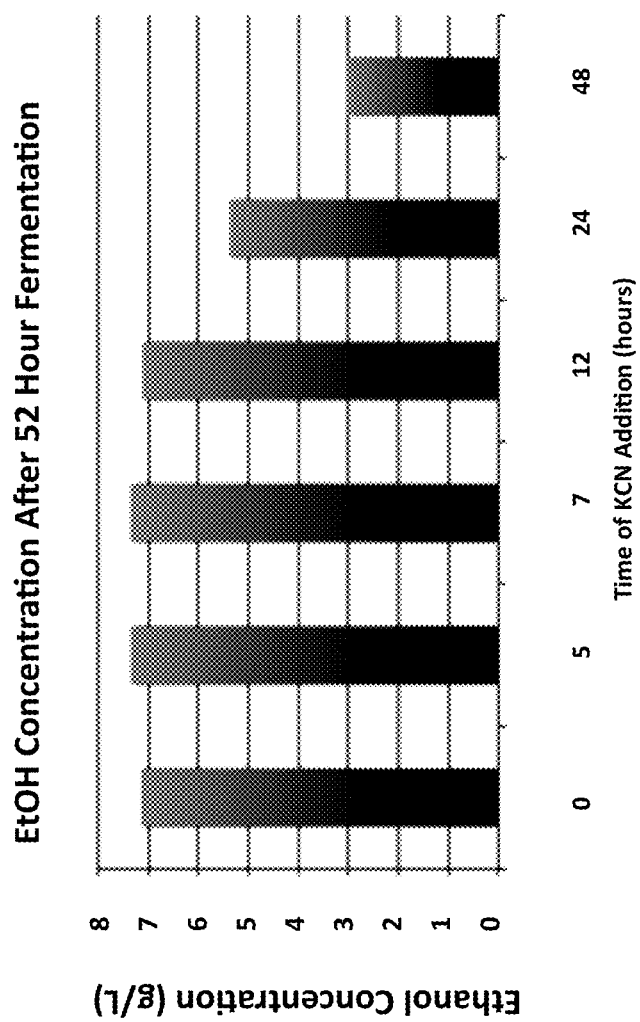
FIG. 5a is a diagram showing rho+ yeast cultured in rich glucose media in the presence of 2.5 mM potassium cyanide (KCN), a respiratory inhibitor showing ethanol production at end of fermentation.

FIG. 5a provides a graph showing ethanol concentrations at 52 hours of fermentation. As shown in FIG. 5a, rho⁺ yeast cultured in rich glucose media in the presence of the respiratory inhibitor 2.5 mM potassium cyanide (KCN) enhanced ethanol production at end of fermentation for cultures with KCN added within 12 hours of fermentation being initiated.

Figure 5B:
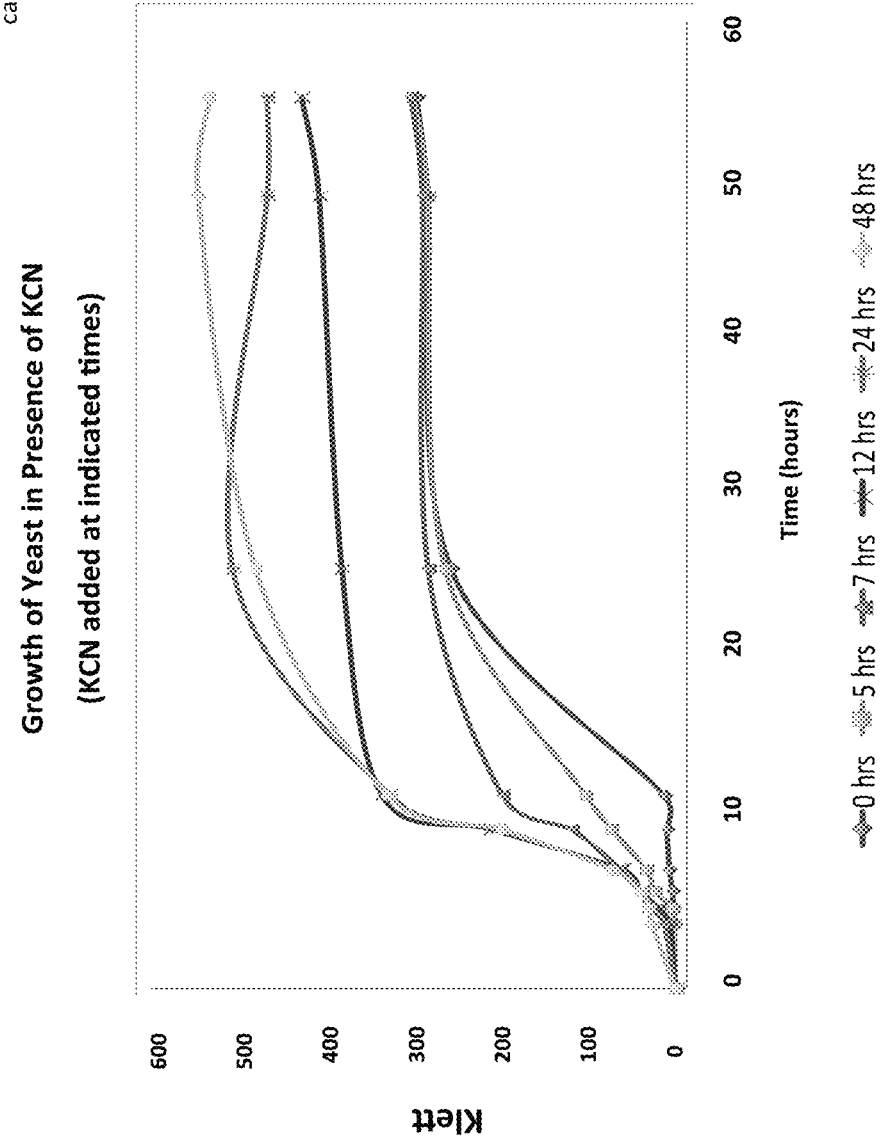
FIG. 5b is a diagram showing rho+ yeast cultured in rich glucose media in the presence of 2.5 mM potassium cyanide (KCN), a respiratory inhibitor showing growth curves for yeast cultures that have been treated with KCN at the indicated points in their fermentations.

As shown in FIG. 5b, rho⁺ yeast cultured in rich glucose media in the presence of 2.5 mM potassium cyanide (KCN), a respiratory inhibitor, show reduced growth for yeast cultures that have been treated with KCN at the indicated points in their fermentations.

Yeast strains compromised for respiratory function exhibit decreased growth rate, loss of viability upon carbon source depletion, desiccation and increased sensitivity to reactive oxygen species (Francis et al. 2007; Ocampo et al. 2012; Calahan et al. 2011; Grant et al. 1997. *FEBS Lett,* 410(2-3), pp. 219-222). All of these present significant hurdles in industrial settings. Thus, creating the ability to support respiration during preparatory phases of the production cycle (to enhance growth), but block it during fermentation (to enhance production efficiency) will provide the best of both worlds for the fermentation industry.

The methods described herein fulfill the requirements of both producers of fermentation products (e.g.—biofuels) and companies that produce yeast for industrial fermentations. The large quantities of yeast that are added to industrial fermentation tanks are produced under aerobic conditions, in contrast to the anaerobic environment used in later steps of biofuel or bio-based chemical production. The methods described herein create yeast in which respiratory capacity is regulated by an anaerobic switch. These yeast will remain respiration competent in the presence of oxygen, allowing production and amplification in the same fashion and with the same yield as is presently used. Upon transfer to production fermentation tanks, the anaerobic conditions will induce the loss of all respiratory capacity, leading to enhanced fermentation efficiency.

The methods described herein also allow for the phenotypic analyses of commercial yeast strains bearing anaerobically expressed inhibitors of mitochondrial respiratory activity.

To determine the relative fermentative efficiency of yeast bearing an anaerobically-induced mitochondrially targeted restriction enzyme, yeast strains either containing or lacking mitochondrial DNA (respiring or non-respiring) and a yeast strain that contains the anaerobically induced mitochondrially-targeted restriction enzyme (mtRE) are cultured on rich glucose media under various growth conditions. Three different features of the individual fermentations are then measured.

First, the rate of growth of each strain in the different conditions will be determined by measuring the increase in growth using a Klett meter (light scattering).

Second, biomass accumulation at the end of fermentation (stationary phase) will be determined by measuring the dry cell weight of each culture. To determine dry cell weight, duplicate 10-ml samples will be centrifuged in pre-weighed tubes for 10 min at 3,000×g. The resulting cell pellet will be washed twice in distilled water, re-pelleted after each wash, dried at 75° C. for 36 hours, and then weighed.

Third, the ethanol produced as a function of time will be measured using an enzymatic assay kit (R-Biopharm). The enzymatic assay depends on the production of NADH, which is monitored by measuring absorbance at 340 nm, as ethanol is oxidized to acetaldehyde. Similarly, glucose concentration in culture supernatants will be determined by following the enzymatic oxidation of NADH to $NAD^+$ at 340 nm using a Boehringer-Mannheim d-glucose test kit. The production of ethanol occurs at a rate inversely proportional to glucose consumption.

Different growth conditions may be employed, including aerobic culture (aeration through shaking of flasks with baffled bottoms at 300 rpm with atmospheric exposure), semi-anaerobic cultures (shaking at 100 rpm in smooth bottom sealed flasks) and anaerobic culture (culturing in media that has been flushed with $N_2$ and grown in sealed tubes that are slowly mixed) and incubation at 30 and 35°. Fermentation outcomes are compared in media containing different concentrations of glucose: high (100 g/L), medium (20 g/L), and low (5 g/L). Fermentation progress and outcomes may also be monitored at normal pH (6.0) and at low pH (4.0). The ability to ferment effectively at lower pH is important as lignocellulosic hydrolysates are produced using acid, and lower pH fermentation helps prevent contamination by bacteria in commercial settings (Benjaphokee et al. 2012. *New biotechnology*, 29(3), pp. 379-386). Finally, the ability of the altered and control yeast strains to ferment alternative hexoses (galactose) and pentoses (xylose) may be analyzed.

Yeast may be sampled from midpoint and endpoint of each fermentation. Plating efficiencies of yeast on rich glucose media and rich ethanol/glycerol media will allow us to calculate the "$rho^o$ rate" (Hanekamp et al. 2002). This commonly used term reflects the percentage of cells in a culture that are incapable of respiration (growth on ethanol/glycerol media requires functional mitochondrial DNA). Wild-type laboratory strains have a rate that varies from 1 to 5%. The expectation is that yeast bearing the gene fusion that expresses a mitochondrially targeted restriction enzyme will have a 1 to 5% $rho^o$ rate in the presence of oxygen but will be 100% $rho^o$ by the midpoint of an anaerobic fermentation.

Commercial yeast strains may be prepared and shipped to industrial fermentation sites most often as "dry active" yeast—effectively a desiccated preparation of pure yeast. Yeast cultures grown in the fermentation conditions described above will be subjected a "desiccation tolerance test", essentially as described (Welch et al. 2013, *Mol Biol Cell*, 24(2), pp. 115-128). Briefly, yeast from a stationary phase culture grown in the "aerobic" conditions described above will be collected, washed, resuspended in sterile phosphate buffered saline, serially diluted and plated on rich media agar plates to determine the number of viable cells per microliter of culture. A similarly treated aliquot of cells will be lyophilized in a vacuum centrifuge (70 kPa) without heat for approximately 24 hours. The dry yeast will be rehydrated, serially diluted, and plated on rich media agar plates to determine the number of viable cells per microliter of the original culture. A relative score of "desiccation tolerance" for each yeast strain will be assigned by dividing the number of viable yeast per microliter after desiccation by the number of viable yeast in a microliter of culture prior to treatment. The yeast that survive desiccation will be examined for the genetic state of their mtDNA, as evidenced by their ability to grow on nonfermentable carbon sources.

The methods provided herein allow for the modification of yeast strains to enhance the commercial profitability of industrial fermentations used for the production of biofuels and high-value biochemical and pharmaceutical products. The production of ethanol and the consumption of glucose is used as a baseline measurement and as a proxy for the success of fermentation in general. This approach is the appropriate way to determine the commercial efficacy of genetically enhanced yeast strains.

Efforts to enhance the efficiency of yeast fermentation in commercial applications have focused on three different strategies: enhanced tolerance to the product being made (e.g., ethanol or isobutanol), resistance to other environmental stressors such as heat or metabolic poisons present in the lignocellulosic hydrolysate, and the ability to ferment five-carbon sugars that are present in significant amounts in lignocellulosic hydrolysates. Molecular studies of ethanol stress in yeast revealed pleiotropic effects (reviewed in (Stanley et al. 2010. *Journal of applied microbiology*, 109 (1), pp. 13-24), with clear negative impacts on membranes of the secretory system (endoplasmic reticulum, vacuole, and plasma membranes) and on particularly hydrophobic and hydrophilic proteins. Increasing concentrations of ethanol lead to changes in metabolism consistent with loss of enzyme integrity and the induction of heat shock protein expression (X. H. Hu et al. 2007. *Genetics*, 175(3), pp. 1479-1487). Efforts to increase ethanol tolerance in yeast have been three pronged: identifying genes induced upon increasing concentration of ethanol (Teixeira et al. 2009. *Appl. Environ. Microbiol.*, 75(18), pp. 5761-5772; Lewis et al. 2010. *Genetics*, 186(4), pp. 1197-1205.), modifying genes in a directed manner to enhance expression of genes that are highly expressed in ethanol tolerant yeast (Alper et al. 2006. *Science*, 314(5805), pp. 1565-1568), and selecting ethanol-resistant strains after mutagenesis (Abe et al. 2009. *Journal of bioscience and bioengineering,* 108(3), pp. 199-204). Through screening of gene deletion libraries and genomic DNA libraries that overproduce gene products and analysis of evolved yeast strains with enhanced resistance to butanol cellular functions have been identified that are critical for increasing resistance to butanol, isobutanol, and propanol (Ghiaci et al. 2013. *Biotechnology for biofuels,* 6(1), p. 101; González-Ramos et al. 2013. *Biotechnology for biofuels,* 6(1), p. 48).

As used herein "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

A variety of transformation techniques are available and known to those skilled in the art for introduction of constructs into a yeast. As described earlier, all DNA manipulations were performed using standard techniques (Sambrook et al., (1989)). To confirm the presence of the transgenes in yeast, a polymerase chain reaction (PCR) amplification or Southern blot analysis can be performed using methods known to those skilled in the art.

Generally, the DNA that is introduced into an organism is part of a construct, as described in FIGS. 2a and 2b. A construct is an artificially constructed segment of DNA that may be introduced into a target organism tissue or organism cell. Constructs are engineered DNA molecules that encode genes and flanking sequences that enable the constructs to integrate into the host genome at (targeted) locations. The DNA may be a gene of interest, e.g., a coding sequence for a protein, or it may be a sequence that is capable of regulating expression of a gene, such as an antisense sequence, a sense suppression sequence, or a miRNA sequence. As used herein, "gene" refers to a segment of nucleic acid. A gene can be introduced into a genome of a species, whether from a different species or from the same species. The construct typically includes regulatory regions operably linked to the 5' side of the DNA of interest and/or to the 3' side of the DNA of interest. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation. A cassette containing all of these elements is also referred to herein as an expression cassette. The expression cassettes may additionally contain 5' leader sequences in the expression cassette construct. (A leader sequence is a nucleic acid sequence containing a promoter as well as the upstream region of a gene.) The regulatory regions (i.e., promoters, transcriptional regulatory regions, translational regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670 and 2006/0248616. The expression cassette may additionally contain selectable marker genes which will be discussed in more detail later.

The products of the genes are often proteins, but in non-protein coding genes such as rRNA genes or tRNA genes, the product is a functional RNA. The process of gene expression is used by all known life forms, i.e., eukaryotes (including multicellular organisms), prokaryotes (bacteria and archaea), and viruses, to generate the macromolecular machinery for life. Several steps in the gene expression process may be modulated, including the transcription, up-regulation, RNA splicing, translation, and post translational modification of a protein.

A promoter is a DNA region, which includes sequences sufficient to cause transcription of an associated (downstream) sequence. The promoter may be regulated, i.e., not constitutively acting to cause transcription of the associated sequence. If inducible, there are sequences present therein which mediate regulation of expression so that the associated sequence is transcribed only when an inducer molecule is present. The promoter may be any DNA sequence that shows transcriptional activity in the chosen yeast cell. The promoter may be inducible or constitutive. It may be naturally-occurring, may be composed of portions of various naturally-occurring promoters, or may be partially or totally synthetic. Guidance for the design of promoters is derived from studies of promoter structure, such as that of Harley and Reynolds, *Nucleic Acids Res.,* 15, 2343-61 (1987). In addition, the location of the promoter relative to the transcription start may be optimized. Many suitable promoters for use in yeast are well known in the art, as are nucleotide sequences, which enhance expression of an associated expressible sequence.

While the PAU20 gene anaerobic promoter is an example of an inducible promoter that may be used in the methods described herein, a number of promoters may be used herein. Promoters can be selected based on the desired outcome. That is, the nucleic acids can be combined with constitutive, tissue-preferred, or other promoters for expression in the host cell of interest.

More than 280 genome-wide transcription analyses have been performed using yeast and have been compiled and can be probed using various websites. The algorithm used to compile and group genes with similar expression patterns (Anon 2007. Exploring the functional landscape of gene expression: directed search of large microarray compendia, 23(20), pp. 2692-2699) reveals dozens of candidate promoters that are tightly regulated, repressing transcription in the presence of oxygen and inducing expression more than 500-fold in anaerobic conditions. In an effort to design a mitochondrial-targeted restriction enzyme that leads to rho° formation upon anaerobiosis, the promoter of the PAU20 gene will be used. This gene has undetectable levels of transcript in the presence of oxygen and is highly induced when cultured in anaerobic conditions (Luo & van Vuuren 2009. *Microbiology (Reading, England),* 155 (Pt 12), pp. 4036-4049), and unlike some other anaerobically expressed genes has exceptionally low transcriptional response to other environmental stressors.

Restriction Enzymes

Restriction enzymes have been targeted to mitochondria in a number of eukaryotic cells, including yeast (Kalifa et al. 2012. *Genetics,* 190(3), pp. 951-964). Since the mitochondrial genome is A/T rich, the restriction enzyme MseI, recognizing TTAA, will be the first restriction enzyme targeted to the mitochondria and it has 2365 possible cut sites in the reference sequence. MseI is a 186 amino acid protein, allowing the construction of a compact gene fusion (Uniprot accession Q2I0D9). It is important to note that the 69 amino acid ATP9 presequence fused to the restriction enzyme structural gene is largely removed upon entry into the mitochondrial matrix as it is cleaved between amino acids 66 and 67 by the mitochondrial processing protease (Westermann & Neupert 2000. Mitochondria-targeted green fluorescent proteins: convenient tools for the study of organelle biogenesis in *Saccharomyces cerevisiae. Yeast.*), leaving as few as three extra residues added to the amino terminal end of the restriction enzyme.

Yeast Strain Production

Standard genetic techniques are used to construct and analyze the various strains of the present disclosure (see Sherman et al., 1986). *Escherichia coli* strain XL-1 Blue (Stratagene) is used for preparation and manipulation of DNA. Plasmids containing *E. coli* were grown in Luria-Bertani (LB) broth supplemented with 125 µg/ml ampicillin (Sambrook et al., (1989)). Yeast strains are grown in rich glucose medium (YPD) containing 2% glucose, 2% Bacto peptone, 1% yeast extract (Difco), 40 mg/l adenine and 40 mg/l tryptophan; rich ethanol glycerol medium (YPEG) containing 3% ethanol, 3% glycerol, 2% Bacto peptone, 1% yeast extract (Difco), 40 mg/l adenine and 40 mg/l tryptophan; rich raffinose medium (YPR) in which filter sterilized raffinose replaced glucose in the YPD formulation; synthetic glucose medium (SD) containing 2% glucose, 6.7 g/l Yeast Nitrogen Base without amino acids (Difco) supplemented with appropriate nutrients; synthetic ethanol glycerol medium (SEG) containing 3% ethanol, 3% glycerol, 6.7 g/l Yeast Nitrogen Base without amino acids (Difco) supplemented with appropriate nutrients; and sporulation medium (SPO) containing 1% potassium acetate supplemented with the complete set of nutrients. The complete set of nutrients is uracil 40 mg/l, adenine 40 mg/l, tryptophan 40 mg/l, lysine 60 mg/l, leucine 100 mg/l, histidine 20 mg/l, isoleucine 30 mg/l, and valine 150 mg/l. For plates, bacteriological agar (US Biological) was added at 15 g/l. Where indicated, ethidium bromide (EtBr) is added at 25 µg/ml and geneticin at 300 µg/ml, or nourseothricin (Werner Bioagents) is top spread on plates at 25 µg/ml. All yeast media are incubated at 30° C. except SPO, which is incubated at room temperature. LB medium is incubated at 37° C.

Vector Construction, Transformation, and Heterologous Protein Expression

As used herein plasmid, vector or cassette refers to an extrachromosomal element often carrying genes and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with an appropriate 3' untranslated sequence into a cell.

While one example of an expression vector is the recombinant vector of FIGS. 2a and 2b, derivatives of the vectors described herein may be capable of stable transformation of many yeast cells. Vectors for stable transformation of yeast are well known in the art and can be obtained from commercial vendors or constructed from publicly available sequence information. Expression vectors can be engineered to produce heterologous and/or homologous protein(s) of interest (e.g., antibodies, mating type agglutinins, etc.). Such vectors are useful for recombinantly producing the protein of interest and for modifying the natural phenotype of host cells.

To construct the vector, the upstream DNA sequences of a gene expressed under control of a suitable promoter may be restriction mapped and areas important for the expression of the protein characterized. The exact location of the start codon of the gene is determined and, making use of this information and the restriction map, a vector may be designed for expression of a heterologous protein by removing the region responsible for encoding the gene's protein but leaving the upstream region found to contain the genetic material responsible for control of the gene's expression. A synthetic oligonucleotide is inserted in the location where the protein sequence once was, such that any additional gene could be cloned in using restriction endonuclease sites in the synthetic oligonucleotide (i.e., a multicloning site). Publicly available restriction proteins may be used for the development of the constructs. An unrelated gene (or coding sequence) inserted at this site would then be under the control of an extant start codon and upstream regulatory region that will drive expression of the foreign (i.e., not normally present) protein encoded by this gene. Once the gene for the foreign protein is put into a cloning vector, it can be introduced into the host organism using any of several methods, some of which might be particular to the host organism. Variations on these methods are described in the general literature. Manipulation of conditions to optimize transformation for a particular host is within the skill of the art.

To confirm the presence of the transgenes in transgenic cells, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. Once transgenic organisms have been obtained, they may be grown to produce organisms or parts having the desired phenotype.

Selectable Markers

A selectable marker (SM) such as the KAN-MX gene of the construct of FIGS. 2a and 2b, can provide a means to identify yeast cells that express a desired product. Selectable markers include, but are not limited to, ampicillin resistance for prokaryotes such as *E. coli*, neomycin phosphotransferase, which confers resistance to the aminoglycosides neomycin, kanamycin and paromycin (Herrera-Estrella, *EMBO J.* 2:987-995, (1983)); dihydrofolate reductase, which confers resistance to methotrexate (Reiss, *Plant Physiol. (Life Sci. Adv.)* 13:143-149, (1994)); trpB, which allows cells to utilize indole in place of tryptophan; hisD, which allows cells to utilize histinol in place of histidine (Hartman, *Proc. Natl. Acad. Sci., USA* 85:8047, (1988)); mannose-6-phosphate isomerase which allows cells to utilize mannose (WO 94/20627); hygro, which confers resistance to hygromycin (Marsh, *Gene* 32:481-485, (1984)); ornithine decarboxylase, which confers resistance to the ornithine decarboxylase inhibitor, 2-(difluoromethyl)-DL-ornithine (DFMO; McConlogue, In: *Current Communications in Molecular Biology*, Cold Spring Harbor Laboratory ed., (1987)); deaminase from *Aspergillus terreus*, which confers resistance to Blasticidin S (Tamura, *Biosci. Biotechnol. Biochem.* 59:2336-2338, (1995)); phosphinothricin acetyltransferase gene, which confers resistance to phosphinothricin (White et al., *Nucl. Acids Res.* 18:1062, (1990); Spencer et al., *Theor. Appl. Genet.* 79:625-633, (1990)); a mutant acetolactate synthase, which confers imidazolione or sulfonylurea resistance (Lee et al., *EMBO J.* 7:1241-1248, (1988)), a mutant EPSPV-synthase, which confers glyphosate resistance (Hinchee et al., *BioTechnology* 91:915-922, (1998)); a mutant psbA, which confers resistance to atrazine (Smeda et al., *Plant Physiol.* 103:911-917, (1993)), a mutant protoporphyrinogen oxidase (see U.S. Pat. No. 5,767,373), or other markers conferring resistance to an herbicide such as glufosinate.

Transcription Terminator

The transcription termination region of the constructs is a downstream regulatory region including the stop codon and the transcription terminator sequence. Alternative transcription termination regions that may be used may be native with the transcriptional initiation region, may be native with the DNA sequence of interest, or may be derived from another source. The transcription termination region may be naturally occurring, or wholly or partially synthetic.

The practice described herein employs, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, et al., *Molecular Cloning*, Cold Spring Harbor Laboratory Press, Cold Spring Harbor, N.Y. (1982); Sambrook, et al., (1989); Sambrook and Russell, *Molecular Cloning*, 3rd Ed., Cold Spring Harbor Laboratory Press, Cold Spring Harbor, N.Y. (2001); Ausubel, et al., *Current Protocols in Molecular Biology*, John Wiley & Sons (including periodic updates) (1992); Glover, *DNA Cloning*, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, NY (1992); Guthrie and Fink, *Guide to Yeast Genetics and Molecular Biology*, Academic Press, NY (1991); Harlow and Lane, *Antibodies*, Cold Spring Harbor Laboratory Press, Cold Spring Harbor, N.Y. (1988); *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, A. R. Liss, Inc. (1987); *Immobilized Cells And Enzymes*, IRL Press (1986); B. Perbal, *A Practical Guide To Molecular Cloning* (1984); the treatise, *Methods In Enzymology*, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, *Essential Immunology*, 6th Edition, Blackwell Scientific Publications, Oxford (1988); Fire, et al., *RNA Interference Technology: From Basic Science to Drug Development*, Cambridge University Press, Cambridge (2005); Schepers, *RNA Interference in Practice*, Wiley-VCH (2005); Engelke, *RNA Interference (RNAi): The Nuts & Bolts of siRNA Technology*, DNA Press (2003); Gott, *RNA Interference, Editing, and Modification: Methods and Protocols (Methods in Molecular Biology)*, Human Press, Totowa, N.J. (2004); and Sohail, *Gene Silencing by RNA Interference: Technology and Application*, CRC (2004)).

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The use of the terms "a," "an," and "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

What is claimed is:

1. A method for enhanced fermentation through the genetic modification of yeast comprising:

stably integrating into a yeast an oxygen dependent inducible promoter coding sequence, wherein said inducible promoter coding sequence is an anaerobic promoter selected from PAU20, DAN1, ANB1, and ROX1, wherein said anaerobic promoter is operably linked to at least one restriction enzyme coding sequence or an RNAse Barnase coding sequence, wherein said at least one restriction enzyme is chosen from EcoR1, ScaI and MseI;

wherein when oxygen levels around said yeast reach zero, said oxygen dependent inducible promoter coding sequence induces expression of the at least one restriction enzyme or RNAse Barnase, wherein said at least one restriction enzyme or RNAse Barnase targets and destroys the mitochondrial DNA within the mitochondria of the yeast, thereby destroys mitochondria-8, replace -a sequence- with -the sequence-, thereby destroying the mitochondria; and wherein said destruction of said mitochondria induces enhanced fermentation by said yeast.

2. The method of claim 1, further comprising a selectable marker.

3. The method of claim 2, wherein said selectable marker is a drug resistance selectable marker.

4. The method of claim 3, wherein said selectable marker is the KAN-MX gene.

* * * * *

UNITED STATES PATENT AND TRADEMARK OFFICE
CERTIFICATE OF CORRECTION

PATENT NO. : 9,932,608 B2
APPLICATION NO. : 14/558124
DATED : April 3, 2018
INVENTOR(S) : Peter E. Thorsness and Elizabeth A. Hiatt It is certified that error appears in the above-identified patent and that said Letters Patent is hereby corrected as shown below:

Column 16, Lines 51-52, in Claim 1: After "yeast," delete "thereby destroys mitochondria-8, replace -a sequence-with -the sequence-,"

Signed and Sealed this
Third Day of July, 2018

Andrei Iancu
*Director of the United States Patent and Trademark Office*